(12) United States Patent
Ralston

(10) Patent No.: US 10,624,613 B2
(45) Date of Patent: Apr. 21, 2020

(54) ULTRASOUND SIGNAL PROCESSING CIRCUITRY AND RELATED APPARATUS AND METHODS

(71) Applicant: Butterfly Network, Inc., Guilford, CT (US)

(72) Inventor: Tyler S. Ralston, Clinton, CT (US)

(73) Assignee: Butterfly Network, Inc., Guilford, CT (US)

( * ) Notice: Subject to any disclaimer, the term of this patent is extended or adjusted under 35 U.S.C. 154(b) by 1062 days.

(21) Appl. No.: 14/997,381

(22) Filed: Jan. 15, 2016

(65) Prior Publication Data

US 2017/0202541 A1    Jul. 20, 2017

(51) Int. Cl.
| | |
|---|---|
| *A61B 8/00* | (2006.01) |
| *A61B 8/08* | (2006.01) |
| *G01S 15/89* | (2006.01) |
| *G01S 7/52* | (2006.01) |

(52) U.S. Cl.
CPC .......... *A61B 8/5207* (2013.01); *A61B 8/4494* (2013.01); *G01S 7/5208* (2013.01); *G01S 15/8915* (2013.01); *G01S 15/8977* (2013.01); *G01S 7/52034* (2013.01)

(58) Field of Classification Search
CPC .......... A61B 8/08; A61B 8/00; A61B 8/5207; A61B 8/4494; G01S 7/5208; G01S 7/52034; G01S 15/8915; G01S 15/8977; A61L 38/4494
See application file for complete search history.

(56) References Cited

U.S. PATENT DOCUMENTS

| | | | |
|---|---|---|---|
| 5,844,445 A | 12/1998 | Takeyari | |
| 6,278,890 B1 * | 8/2001 | Chassaing | A61B 7/00 600/407 |
| 6,434,583 B1 * | 8/2002 | Dapper | G06F 17/14 708/409 |
| 7,313,053 B2 | 12/2007 | Wodnicki | |
| 7,549,961 B1 | 6/2009 | Hwang | |
| 8,852,103 B2 | 10/2014 | Rothberg et al. | |
| 9,229,097 B2 | 1/2016 | Rothberg et al. | |
| 9,473,136 B1 | 10/2016 | Chen et al. | |
| 9,492,144 B1 | 11/2016 | Chen et al. | |

(Continued)

FOREIGN PATENT DOCUMENTS

| | | |
|---|---|---|
| CN | 103607130 A | 2/2014 |
| TW | 201445554 A | 12/2014 |

(Continued)

OTHER PUBLICATIONS

International Search Report and Written Opinion dated Nov. 13, 2014 for Application No. PCT/US2014/032803.

(Continued)

*Primary Examiner* — Bill Thomson
*Assistant Examiner* — Amy J Shafqat
(74) *Attorney, Agent, or Firm* — Wolf, Greenfield & Sacks, P.C.

(57) ABSTRACT

Ultrasound signal processing circuitry and related apparatus and methods are described. Groups of signal samples corresponding to respective acquisitions performed by an ultrasound transducer array may be processed by being transformed to the Fourier domain and via the application of one or more weighting functions. The transformed groups of signals may be combined with one another in the Fourier domain to obtain a Fourier-compounded set of signals that may be used for image formation.

16 Claims, 8 Drawing Sheets

(56) References Cited

U.S. PATENT DOCUMENTS

| | | | |
|---|---|---|---|
| 9,705,518 | B2 | 7/2017 | Chen et al. |
| 9,933,516 | B2 | 4/2018 | Chen et al. |
| 9,958,537 | B2 | 5/2018 | Chen et al. |
| 10,014,871 | B2 | 7/2018 | Chen et al. |
| 10,082,488 | B2 | 9/2018 | Chen et al. |
| 10,175,347 | B2 | 1/2019 | Chen et al. |
| 10,187,020 | B2 | 1/2019 | Chen et al. |
| 10,277,236 | B2 | 4/2019 | Chen et al. |
| 2003/0097071 | A1 | 5/2003 | Halmann et al. |
| 2007/0001764 | A1 | 1/2007 | Huang et al. |
| 2007/0242567 | A1 | 10/2007 | Daft et al. |
| 2009/0036772 | A1 | 2/2009 | Lu |
| 2009/0250729 | A1 | 10/2009 | Lemmerhirt et al. |
| 2010/0152587 | A1 | 6/2010 | Haider et al. |
| 2010/0317972 | A1 | 12/2010 | Baumgartner et al. |
| 2013/0172752 | A1 | 7/2013 | Hu et al. |
| 2013/0253325 | A1 | 9/2013 | Call et al. |
| 2014/0078866 | A1 | 3/2014 | Kanamori et al. |
| 2014/0200456 | A1 | 7/2014 | Owen |
| 2014/0288428 | A1 | 9/2014 | Rothberg et al. |
| 2015/0032002 | A1 | 1/2015 | Rothberg et al. |
| 2015/0297193 | A1 | 10/2015 | Rothberg et al. |
| 2015/0301167 | A1* | 10/2015 | Sentelle ............... A61B 5/0205 342/22 |
| 2017/0160239 | A1 | 6/2017 | Chen et al. |
| 2017/0160387 | A1 | 6/2017 | Chen et al. |
| 2017/0160388 | A1 | 6/2017 | Chen et al. |
| 2017/0163225 | A1 | 6/2017 | Chen et al. |
| 2017/0163276 | A1 | 6/2017 | Chen et al. |
| 2017/0264307 | A1 | 9/2017 | Chen et al. |
| 2017/0307739 | A1 | 10/2017 | Chen et al. |
| 2017/0307741 | A1* | 10/2017 | Ralston ................. G01S 7/5202 |
| 2018/0210073 | A1 | 7/2018 | Chen et al. |
| 2018/0262200 | A1 | 9/2018 | Chen et al. |
| 2018/0364200 | A1 | 12/2018 | Chen et al. |
| 2019/0086525 | A1 | 3/2019 | Chen et al. |
| 2019/0140603 | A1 | 5/2019 | Chen et al. |

FOREIGN PATENT DOCUMENTS

| | | |
|---|---|---|
| WO | WO 2004/061575 A2 | 7/2004 |
| WO | WO 2009/135255 A1 | 11/2009 |
| WO | WO 2011/163475 A1 | 12/2011 |

OTHER PUBLICATIONS

International Search Report and Written Opinion dated Jan. 12, 2017 for Application No. PCT/US2016/058033.

International Preliminary Report on Patentability dated Jul. 26, 2018 in connection with International Application No. PCT/US2016/058033.

Taiwanese Office Action dated Jan. 19, 2018 in connection with Taiwanese Application No. 105139662.

Agarwal et al., Single-Chip Solution for Ultrasound Imaging Systems: Initial Results. 2007 IEEE Ultrasonics Symposium. Oct. 1, 2007;1563-6.

Chen et al., Ultrasonic Imaging Front-End Design for CMUT: A 3-Level 30Vpp Pulse-Shaping Pulser with Improved Efficiency and a Noise-Optimized Receiver. IEEE Asian Solid-State Circuits Conference. Nov. 12-14, 2012;173-6.

Cheng et al., An Efficient Electrical Addressing Method Using Through-Wafer Vias for Two-Dimensional Ultrasonic Arrays. 2000 IEEE Ultrasonics Symposium. 2000;2:1179-82.

Cheng et al., CMUT-in-CMOS ultrasonic transducer arrays with on-chip electronics. Transducers 2009. IEEE. Jun. 21, 2009;1222-5.

Cheng et al., Electrical Through-Wafer Interconnects with Sub-PicoFarad Parasitic Capacitance. 2001 Microelectromechan Syst Conf. Aug. 24, 2001;18-21.

Daft et al., 5F-3 A Matrix Transducer Design with Improved Image Quality and Acquisition Rate. 2007 IEEE Ultrasonics Symposium. Oct. 1, 2007;411-5.

Daft et al., Microfabricated Ultrasonic Transducers Monolithically Integrated with High Voltage Electronics. 2004 IEEE Ultrasonics Symposium. Aug. 23, 2004;1:493-6.

Gurun et al., Front-end CMOS electronics for monolithic integration with CMUT arrays: circuit design and initial experimental results. Proc Ultrason Symp. 2008;390-3.

Khuri-Yakub et al., Miniaturized Ultrasound Imaging Probes Enabled by CMUT Arrays with Integrated Frontend Electronic Circuits. Conf Proc IEEE Eng Med Biol Soc. 2010;1:5987-90. doi:10.1109/IEMBS.2010.5627580. Epub Dec. 6, 2010. 13 pages.

Kim et al., Design and Test of a Fully Controllable 64x128 2-D CMUT Array Integrated with Reconfigurable Frontend ASICs for Volumetric Ultrasound Imaging. IEEE. International Ultrasonics Symposium Proceedings. Oct. 7-10, 2012;77-80. doi: 10.1109/ULTSYM.2012.0019.

Extended European Search Report dated Jul. 22, 2019 in connection with European Application No. 16885387.7.

Wang, Two-Dimensional Fourier Transform. Nov. 15, 2007; 6 pages. Retrieved from the Internet: URL:http://fourier.eng.hmc.edu/e101/lectures/Image_Processing_node6.html [retrieved on Jul. 12, 2019].

* cited by examiner

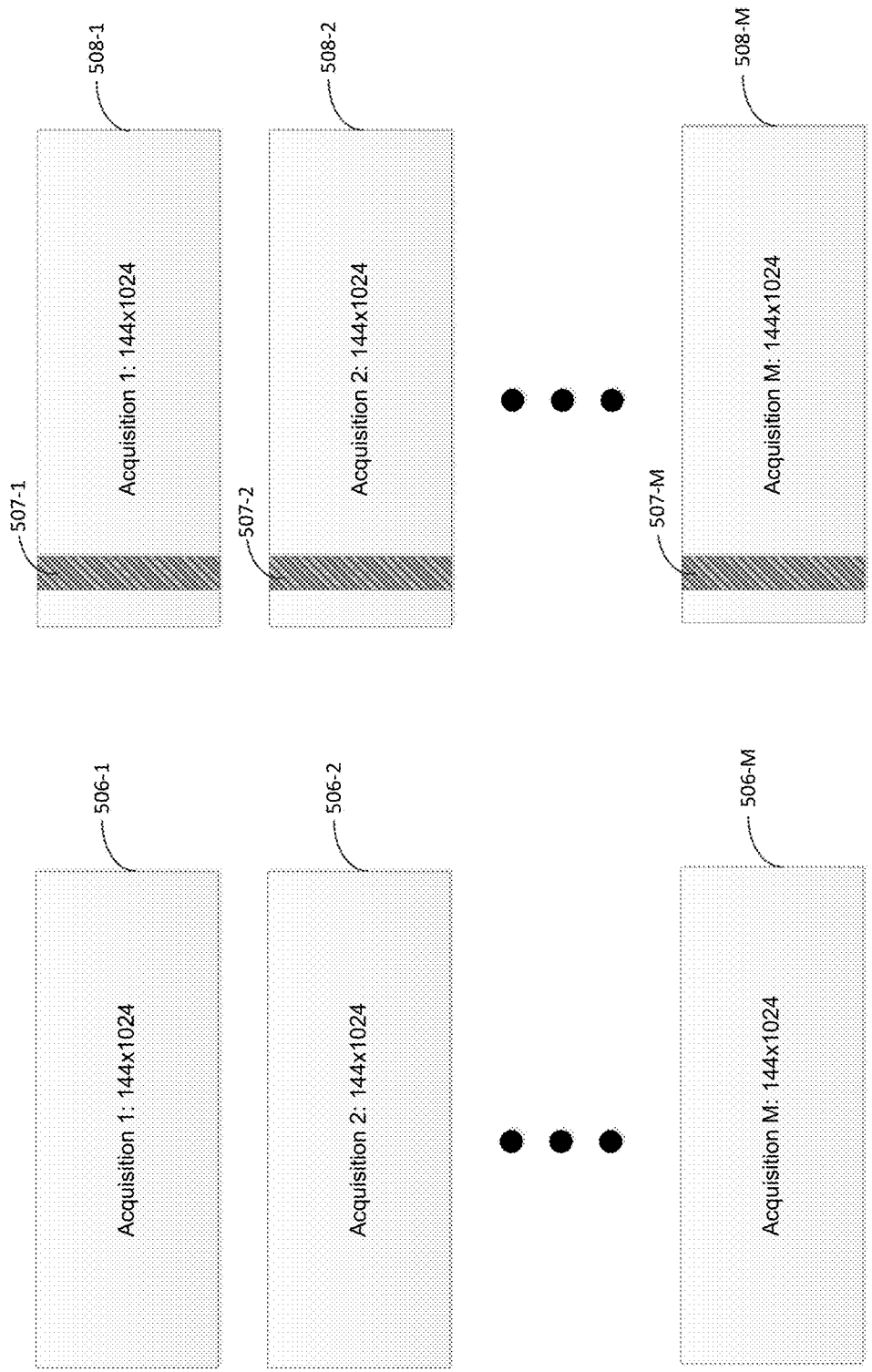

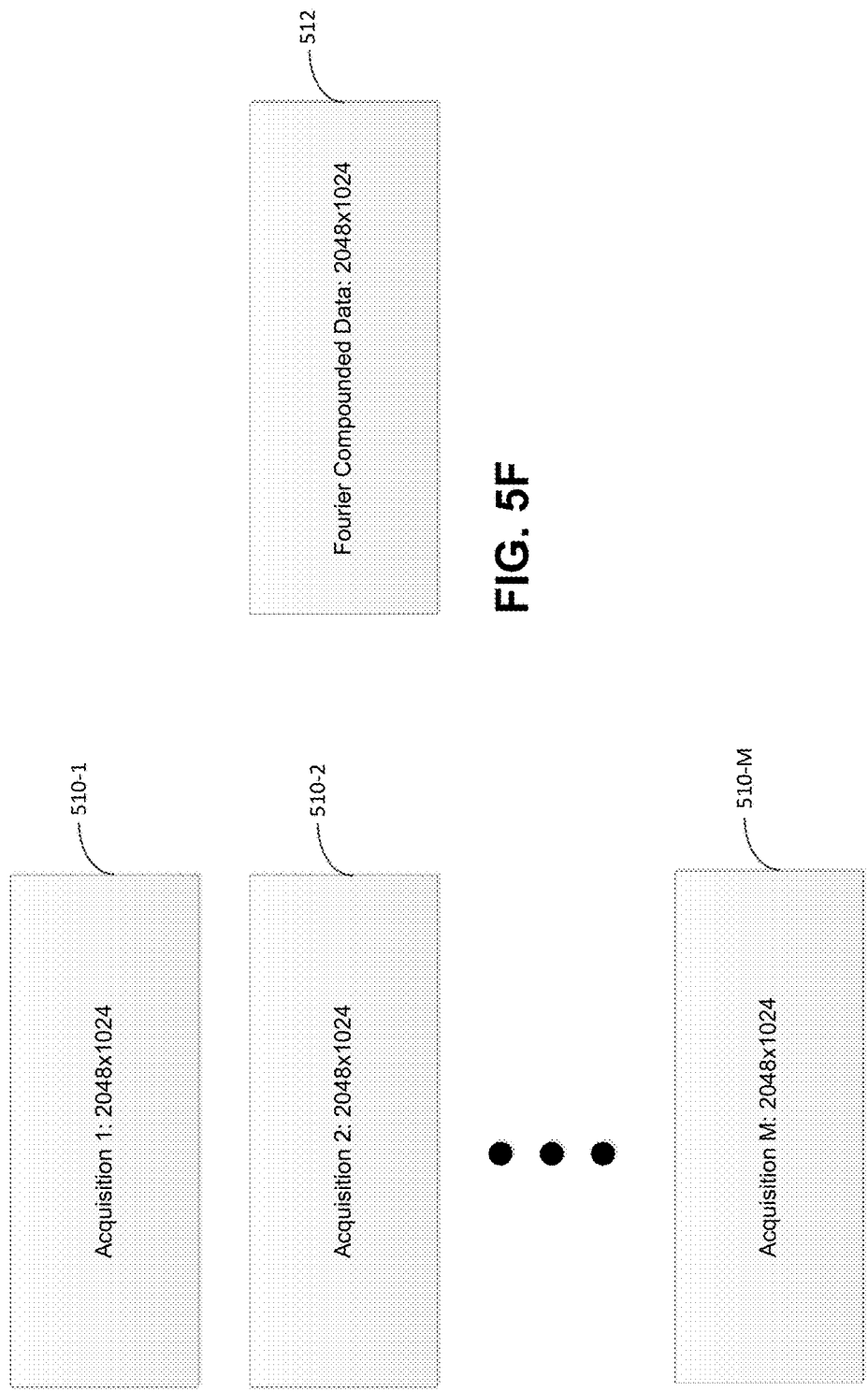

US 10,624,613 B2

ULTRASOUND SIGNAL PROCESSING CIRCUITRY AND RELATED APPARATUS AND METHODS

FIELD

Aspects of the present disclosure relate to ultrasound signal processing circuitry, and to related ultrasound apparatus and methods.

BACKGROUND

Ultrasound transducer arrays used for medical applications typically produce a large amount of data, as needed to produce ultrasound images for medical applications. The higher the quality and complexity of the desired images, the more data is typically needed.

The problem of transporting multiple channels of analog signals from an ultrasound transducer array to the control and processing electronics of an ultrasound system has limited the utility of the larger and denser arrays of transducers needed to improve the resolution of ultrasound imaging and to enable high quality 3D volumetric imaging.

SUMMARY

The present disclosure describes aspects of processing signals received from an ultrasound transducer array in an ultrasound transducer based imaging system, including the digital and analog circuitry used to process the signals. The digital circuitry includes receive circuitry configured to perform Fourier-domain compounding of ultrasound signals corresponding to different acquisitions of data performed by the ultrasound transducer array.

Some embodiments are directed to an ultrasound device. The ultrasound device comprises a semiconductor die, a plurality of micromachined ultrasonic transducer elements integrated on the semiconductor die and configured to output electrical signals in response to detecting ultrasound signals, and receive circuitry coupled to the plurality of micromachined ultrasonic transducer elements. The receive circuitry is configured to: obtain, based on first electrical signals provided by the plurality of micromachined ultrasonic transducer elements, a first set of signal samples representing a first acquisition; obtain, based on second electrical signals provided by the plurality of micromachined ultrasonic transducer elements, a second set of signal samples representing a second acquisition; apply a Fourier transformation to the first set of signal samples to generate a first Fourier-transformed set of signals and to the second set of signal samples to generate a second Fourier-transformed set of signals; and generate a Fourier-compounded set of signals at least in part by combining the first and second Fourier-transformed sets of signals.

Some embodiments provide for a method performed by an ultrasound device comprising a semiconductor die, a plurality of micromachined ultrasonic transducer elements integrated on the semiconductor die and configured to output electrical signals in response to detecting ultrasound signals, and receive circuitry coupled to the plurality of micromachined ultrasonic transducer elements. The method comprises using the receive circuitry to perform: obtaining, based on first electrical signals provided by the plurality of micromachined ultrasonic transducer elements, a first set of signal samples representing a first acquisition; obtaining, based on second electrical signals provided by the plurality of micromachined ultrasonic transducer elements, a second set of signal samples representing a second acquisition; applying a Fourier transformation to the first set of signal samples to generate a first Fourier-transformed set of signals and to the second set of signal samples to generate a second Fourier-transformed set of signals; and generating a Fourier-compounded set of signals at least in part by combining the first and second Fourier-transformed sets of signals.

BRIEF DESCRIPTION OF THE DRAWINGS

Various aspects and embodiments of the disclosed technology will be described with reference to the following figures. It should be appreciated that the figures are not necessarily drawn to scale. Items appearing in multiple figures are indicated by the same reference number in all the figures in which they appear.

FIGS. 5A-5F illustrate processing performed by the digital processing block of the RX circuitry, in accordance with some embodiments of the technology described herein.

DETAILED DESCRIPTION

Figure 1:
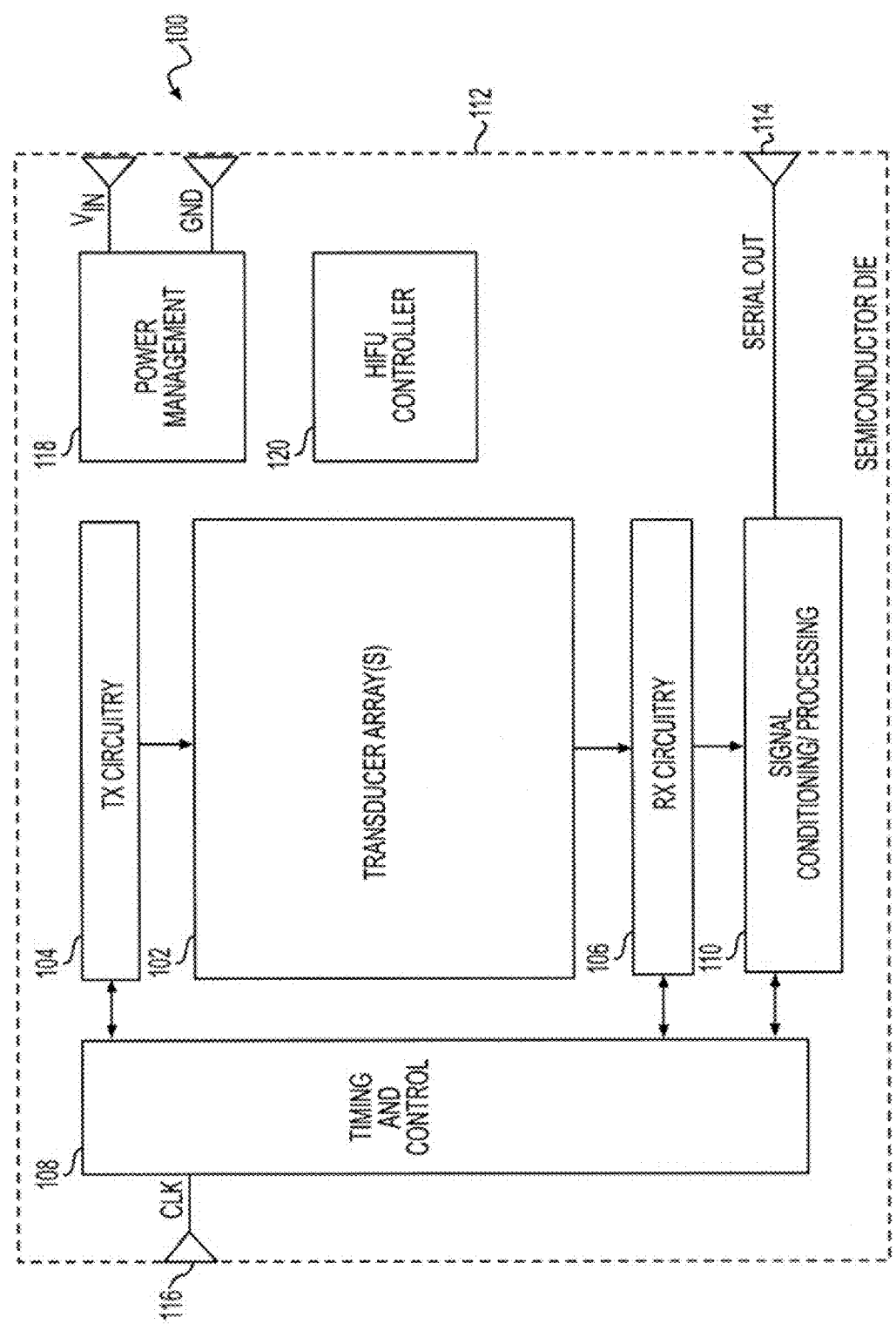
FIG. 1 is a block diagram of an illustrative example of a monolithic ultrasound device embodying various aspects of the disclosed technology.

Aspects of the present disclosure relate to digital signal processing of signals received from an ultrasound transducer array. In some embodiments, the ultrasound transducer array and the circuitry may be integrated on a single complementary metal oxide semiconductor (CMOS) chip, or substrate, or may be on multiple chips within an ultrasound probe. The present disclosure provides unique, cost-effective, and scalable integrated signal processing architectures to process signals from ultrasound transducer elements or groups of ultrasound transducer elements and to provide data that is sufficiently robust for advanced high quality imaging applications. Thus, aspects of the present disclosure provide an architecture which may be used with a single substrate ultrasound device having integrated ultrasound transducers (e.g. CMOS ultrasonic transducers) and digital circuitry.

The present disclosure describes aspects of processing signals received from an ultrasound transducer array in an ultrasound transducer-based imaging system. In particular, the present disclosure describes aspects of processing groups of signals corresponding to respective acquisitions performed by the ultrasound transducer array. Groups of electrical signals corresponding to respective acquisitions performed by the ultrasound transducer array may be processed using analog circuitry and sampled to obtain groups of digital signal samples. In turn, groups of digital signal samples may be processed by digital circuitry at least in part by being transformed to the Fourier domain and, optionally, via the application of one or more weighting functions. The transformed groups of signals may be combined with one another in the Fourier domain to obtain a Fourier-compounded set of signals that may be used for image formation.

Conventional approaches to ultrasound image formation using data obtained over multiple acquisitions compound the data in the time domain. By contrast, the Fourier-domain compounding techniques described herein allow for conditioning of the obtained signals in the Fourier domain prior to compounding the signals, which results in higher quality ultrasound imagery.

Accordingly, in some embodiments, multiple sets of signal samples are obtained from electrical signals gathered by ultrasonic transducers during multiple respective acquisitions. After optional data reduction and time-domain conditioning, each of the multiple sets of signal samples may be transformed into the Fourier domain, where after application of frequency-domain conditioning, the transformed sets of signal samples may be compounded in the Fourier domain to obtain Fourier-compounded data for use in ultrasound image formation.

In some embodiments, a set of signal samples corresponding to an acquisition may be transformed to the Fourier domain in two stages. A one-dimensional fast Fourier transform (FFT) is applied to the set of signal samples in each of the two stages. The set of signal samples may comprise multiple groups of signal samples with each of the multiple groups corresponding to a channel. In the first stage, a one-dimensional FFT is applied to each of the multiple groups of signal samples with respect to time. The complex-valued data obtained as a result of the processing performed by the first stage includes multiple groups of complex values, each of the multiple groups of complex values corresponding to a respective frequency bin in a plurality of frequency bins. In the second stage, a one-dimensional FFT is applied to each of the multiple groups of complex values.

The aspects and embodiments described above, as well as additional aspects and embodiments, are described further below. These aspects and/or embodiments may be used individually, all together, or in any combination of two or more, as the technology described herein is not limited in this respect.

FIG. 1 shows an illustrative example of a monolithic ultrasound device 100 embodying various aspects of the technology described herein. As shown, the device 100 may include one or more transducer arrangements (e.g., arrays) 102, transmit (TX) circuitry 104, receive (RX) circuitry 106, a timing & control circuit 108, a signal conditioning/processing circuit 110, a power management circuit 118, and/or a high-intensity focused ultrasound (HIFU) controller 120. In the embodiment shown, all of the illustrated elements are formed on a single semiconductor die 112. It should be appreciated, however, that in alternative embodiments one or more of the illustrated elements may be instead located off-chip. In addition, although the illustrated example shows both TX circuitry 104 and RX circuitry 106, in alternative embodiments only TX circuitry or only RX circuitry may be employed. For example, such embodiments may be employed in a circumstance where one or more transmission-only devices 100 are used to transmit acoustic signals and one or more reception-only devices 100 are used to receive acoustic signals that have been transmitted through or reflected off of a subject being ultrasonically imaged.

It should be appreciated that communication between one or more of the illustrated components may be performed in any of numerous ways. In some embodiments, for example, one or more high-speed busses (not shown), such as that employed by a unified Northbridge, may be used to allow high-speed intra-chip communication or communication with one or more off-chip components.

The one or more transducer arrays 102 may take on any of numerous forms, and aspects of the present technology do not necessarily require the use of any particular type or arrangement of transducer cells or transducer elements. Indeed, although the term "array" is used in this description, it should be appreciated that in some embodiments the transducer elements may not be organized in an array and may instead be arranged in some non-array fashion. In various embodiments, each of the transducer elements in the array 102 may, for example, include one or more capacitive micromachined ultrasonic transducers (CMUTs), one or more CMOS ultrasonic transducers (CUTs), one or more piezoelectric micromachined ultrasonic transducers (PMUTs), and/or one or more other suitable ultrasonic transducer cells. In some embodiments, the transducer elements of the transducer array 102 may be formed on the same chip as the electronics of the TX circuitry 104 and/or RX circuitry 106. The transducer elements 102, TX circuitry 104, and RX circuitry 106 may, in some embodiments, be integrated in a single ultrasound probe. In some embodiments, the single ultrasound probe may be a hand-held probe. In other embodiments, the single ultrasound probe may be embodied in a patch that may be coupled to a patient. The patch may be configured to transmit, wirelessly, data collected by the patch to one or more external devices for further processing.

A CUT may, for example, include a cavity formed in a CMOS wafer, with a membrane overlying the cavity, and in some embodiments sealing the cavity. Electrodes may be provided to create a transducer cell from the covered cavity structure. The CMOS wafer may include integrated circuitry to which the transducer cell may be connected. The transducer cell and CMOS wafer may be monolithically integrated, thus forming an integrated ultrasonic transducer cell and integrated circuit on a single substrate (the CMOS wafer).

The TX circuitry 104 (if included) may, for example, generate pulses that drive the individual elements of, or one or more groups of elements within, the transducer array(s) 102 so as to generate acoustic signals to be used for imaging. The RX circuitry 106, on the other hand, may receive and process electronic signals generated by the individual elements of the transducer array(s) 102 when acoustic signals impinge upon such elements.

In some embodiments, the timing & control circuit 108 may, for example, be responsible for generating all timing and control signals that are used to synchronize and coordinate the operation of the other elements in the device 100. In the example shown, the timing & control circuit 108 is driven by a single clock signal CLK supplied to an input port 116. The clock signal CLK may, for example, be a high-frequency clock used to drive one or more of the on-chip circuit components. In some embodiments, the clock signal CLK may, for example, be a 1.5625 GHz or 2.5 GHz clock used to drive a high-speed serial output device (not shown in FIG. 1) in the signal conditioning/processing circuit 110, or a 20 Mhz or 40 MHz clock used to drive other digital components on the die 112, and the timing & control circuit 108 may divide or multiply the clock CLK, as necessary, to drive other components on the die 112. In other embodiments, two or more clocks of different frequencies (such as those referenced above) may be separately supplied to the timing & control circuit 108 from an off-chip source.

The power management circuit 118 may, for example, be responsible for converting one or more input voltages $V_{IN}$ from an off-chip source into voltages needed to carry out operation of the chip, and for otherwise managing power consumption within the device 100. In some embodiments, for example, a single voltage (e.g., 12V, 80V, 100V, 120V, etc.) may be supplied to the chip and the power management circuit 118 may step that voltage up or down, as necessary, using a charge pump circuit or via some other DC-to-DC voltage conversion mechanism. In other embodiments, multiple different voltages may be supplied separately to the power management circuit 118 for processing and/or distribution to the other on-chip components.

As shown in FIG. 1, in some embodiments, a HIFU controller 120 may be integrated on the die 112 so as to enable the generation of HIFU signals via one or more elements of the transducer array(s) 102. In other embodiments, a HIFU controller for driving the transducer array(s) 102 may be located off-chip, or even within a device separate from the device 100. That is, aspects of the present disclosure relate to provision of ultrasound-on-a-chip HIFU systems, with and without ultrasound imaging capability. It should be appreciated, however, that some embodiments may not have any HIFU capabilities and thus may not include a HIFU controller 120.

Moreover, it should be appreciated that the HIFU controller 120 may not represent distinct circuitry in those embodiments providing HIFU functionality. For example, in some embodiments, the remaining circuitry of FIG. 1 (other than the HIFU controller 120) may be suitable to provide ultrasound imaging functionality and/or HIFU, i.e., in some embodiments the same shared circuitry may be operated as an imaging system and/or for HIFU. Whether or not imaging or HIFU functionality is exhibited may depend on the power provided to the system. HIFU typically operates at higher powers than ultrasound imaging. Thus, providing the system a first power level (or voltage level) appropriate for imaging applications may cause the system to operate as an imaging system, whereas providing a higher power level (or voltage level) may cause the system to operate for HIFU. Such power management may be provided by off-chip control circuitry in some embodiments.

In addition to using different power levels, imaging and HIFU applications may utilize different waveforms. Thus, waveform generation circuitry may be used to provide suitable waveforms for operating the system as either an imaging system or a HIFU system.

In some embodiments, the system may operate as both an imaging system and a HIFU system (e.g., capable of providing image-guided HIFU). In some such embodiments, the same on-chip circuitry may be utilized to provide both functions, with suitable timing sequences used to control the operation between the two modalities.

In the example shown, one or more output ports 114 may output a high-speed serial data stream generated by one or more components of the signal conditioning/processing circuit 110. Such data streams may, for example, be generated by one or more USB 3.0 modules, and/or one or more 10 GB, 40 GB, or 100 GB Ethernet modules, integrated on the die 112. In some embodiments, the signal stream produced on output port 114 can be fed to a computer, tablet, or smartphone for the generation and/or display of 2-dimensional, 3-dimensional, and/or tomographic images. In embodiments in which image formation capabilities are incorporated in the signal conditioning/processing circuit 110, even relatively low-power devices, such as smartphones or tablets which have only a limited amount of processing power and memory available for application execution, can display images using only a serial data stream from the output port 114. As noted above, the use of on-chip analog-to-digital conversion and a high-speed serial data link to offload a digital data stream is one of the features that helps facilitate an "ultrasound on a chip" solution according to some embodiments of the technology described herein.

Devices 100 such as that shown in FIG. 1 may be used in any of a number of imaging and/or treatment (e.g., HIFU) applications, and the particular examples discussed herein should not be viewed as limiting. In one illustrative implementation, for example, an imaging device including an N×M planar or substantially planar array of CMUT elements may itself be used to acquire an ultrasonic image of a subject, e.g., a person's abdomen, by energizing some or all of the elements in the array(s) 102 (either together or individually) during one or more transmit phases, and receiving and processing signals generated by some or all of the elements in the array(s) 102 during one or more receive phases, such that during each receive phase the CMUT elements sense acoustic signals reflected by the subject. In other implementations, some of the elements in the array(s) 102 may be used only to transmit acoustic signals and other elements in the same array(s) 102 may be simultaneously used only to receive acoustic signals. Moreover, in some implementations, a single imaging device may include a P×Q array of individual devices, or a P×Q array of individual N×M planar arrays of CMUT elements, which components can be operated in parallel, sequentially, or according to some other timing scheme so as to allow data to be accumulated from a larger number of CMUT elements than can be embodied in a single device 100 or on a single die 112.

In yet other implementations, a pair of imaging devices can be positioned so as to straddle a subject, such that one or more CMUT elements in the device(s) 100 of the imaging device on one side of the subject can sense acoustic signals generated by one or more CMUT elements in the device(s) 100 of the imaging device on the other side of the subject, to the extent that such pulses were not substantially attenuated by the subject. Moreover, in some implementations, the same device 100 can be used to measure both the scattering of acoustic signals from one or more of its own CMUT elements as well as the transmission of acoustic signals from one or more of the CMUT elements disposed in an imaging device on the opposite side of the subject.

Figure 2:
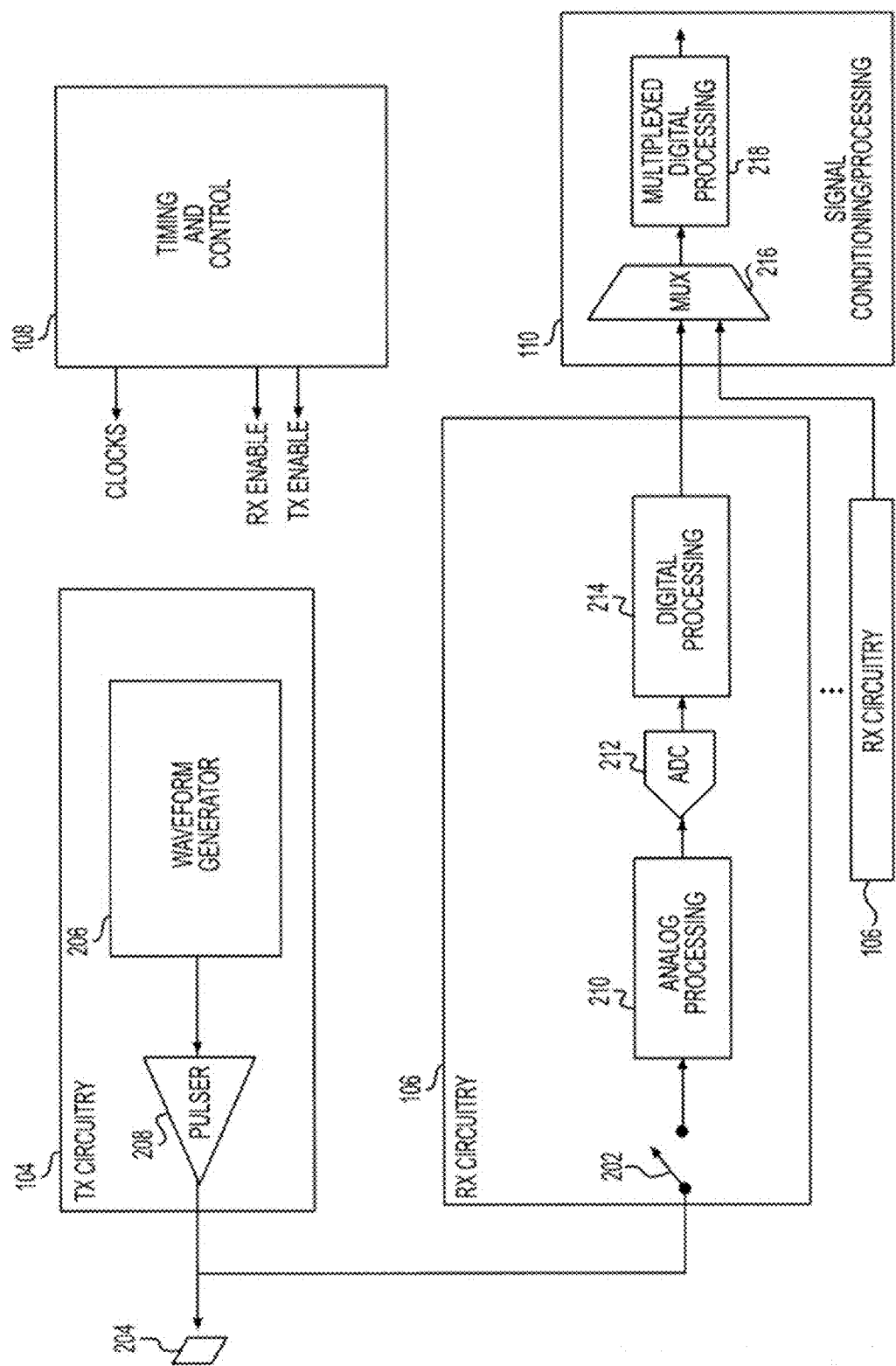
FIG. 2 is a block diagram illustrating how, in some embodiments, the transmit (TX) circuitry and the receive (RX) circuitry for a given transducer element may be used either to energize the element to emit an ultrasonic pulse, or to receive and process a signal from the element representing an ultrasonic pulse sensed by the transducer element.

FIG. 2 is a block diagram illustrating how, in some embodiments, the TX circuitry 104 and the RX circuitry 106 for a given transducer element 204 may be used either to energize the transducer element 204 to emit an ultrasonic pulse, or to receive and process a signal from the transducer element 204 representing an ultrasonic pulse sensed by it. In some implementations, the TX circuitry 104 may be used during a "transmission" phase, and the RX circuitry may be used during a "reception" phase that is non-overlapping with the transmission phase. In other implementations, one of the TX circuitry 104 and the RX circuitry 106 may simply not be used in a given device 100, such as when a pair of ultrasound units is used for only transmissive imaging. As noted above, in some embodiments, a device 100 may alternatively employ only TX circuitry 104 or only RX circuitry 106, and aspects of the present technology do not necessarily require the presence of both such types of circuitry. In various embodiments, TX circuitry 104 and/or RX circuitry 106 may include a TX circuit and/or an RX circuit associated with a single transducer cell (e.g., a CUT or CMUT), a group of two or more transducer cells within a single transducer element 204, a single transducer element 204 comprising a group of transducer cells, a group of two or more transducer elements 204 within an array 102, or an entire array 102 of transducer elements 204.

In the example shown in FIG. 2, the TX circuitry 104/RX circuitry 106 includes a separate TX circuit and a separate RX circuit for each transducer element 204 in the array(s) 102, but there is only one instance of each of the timing & control circuit 108 and the signal conditioning/processing circuit 110. Accordingly, in such an implementation, the timing & control circuit 108 may be responsible for synchronizing and coordinating the operation of all of the TX circuitry 104/RX circuitry 106 combinations on the die 112, and the signal conditioning/processing circuit 110 may be responsible for handling inputs from all of the RX circuitry 106 on the die 112. In other embodiments, timing and control circuit 108 may be replicated for each transducer element 204 or for a group of transducer elements 204.

As shown in FIG. 2, in addition to generating and/or distributing clock signals to drive the various digital components in the device 100, the timing & control circuit 108 may output either an "TX enable" signal to enable the operation of each TX circuit of the TX circuitry 104, or an "RX enable" signal to enable operation of each RX circuit of the RX circuitry 106. In the example shown, a switch 202 in the RX circuitry 106 may always be opened before the TX circuitry 104 is enabled, so as to prevent an output of the TX circuitry 104 from driving the RX circuitry 106. The switch 202 may be closed when operation of the RX circuitry 106 is enabled, so as to allow the RX circuitry 106 to receive and process a signal generated by the transducer element 204.

As shown, the TX circuitry 104 for a respective transducer element 204 may include both a waveform generator 206 and a pulser 208. The waveform generator 206 may, for example, be responsible for generating a waveform that is to be applied to the pulser 208, so as to cause the pulser 208 to output a driving signal to the transducer element 204 corresponding to the generated waveform.

In the example shown in FIG. 2, the RX circuitry 106 for a respective transducer element 204 includes an analog processing block 210, an analog-to-digital converter (ADC) 212, and a digital processing block 214. The ADC 212 may, for example, comprise a 10-bit or 12-bit, 20 Msps, 25 Msps, 40 Msps, 50 Msps, or 80 Msps ADC.

After undergoing processing in the digital processing block 214, the outputs of all of the RX circuits on the die 112 (the number of which, in this example, is equal to the number of transducer elements 204 on the chip) are fed to a multiplexer (MUX) 216 in the signal conditioning/processing circuit 110. In other embodiments, the number of transducer elements is larger than the number of RX circuits, and several transducer elements provide signals to a single RX circuit. The MUX 216 multiplexes the digital data from the RX circuits, and the output of the MUX 216 is fed to a multiplexed digital processing block 218 in the signal conditioning/processing circuit 110, for final processing before the data is output from the die 112, e.g., via one or more high-speed serial output ports 114. The MUX 216 is optional, and in some embodiments parallel signal processing is performed. A high-speed serial data port may be provided at any interface between or within blocks, any interface between chips and/or any interface to a host. Various components in the analog processing block 210 and/or the digital processing block 214 may reduce the amount of data that needs to be output from the die 112 via a high-speed serial data link or otherwise. In some embodiments, for example, one or more components in the analog processing block 210 and/or the digital processing block 214 may thus serve to allow the RX circuitry 106 to receive transmitted and/or scattered ultrasound pressure waves with an improved signal-to-noise ratio (SNR) and in a manner compatible with a diversity of waveforms. The inclusion of such elements may thus further facilitate and/or enhance the disclosed "ultrasound-on-a-chip" solution in some embodiments.

Although particular components that may optionally be included in the analog processing block 210 are described below, it should be appreciated that digital counterparts to such analog components may additionally or alternatively be employed in the digital processing block 214. The converse is also true. That is, although particular components that may optionally be included in the digital processing block 214 are described below, it should be appreciated that analog counterparts to such digital components may additionally or alternatively be employed in the analog processing block 210.

Layout of Ultrasonic Transducers

Figure 3:
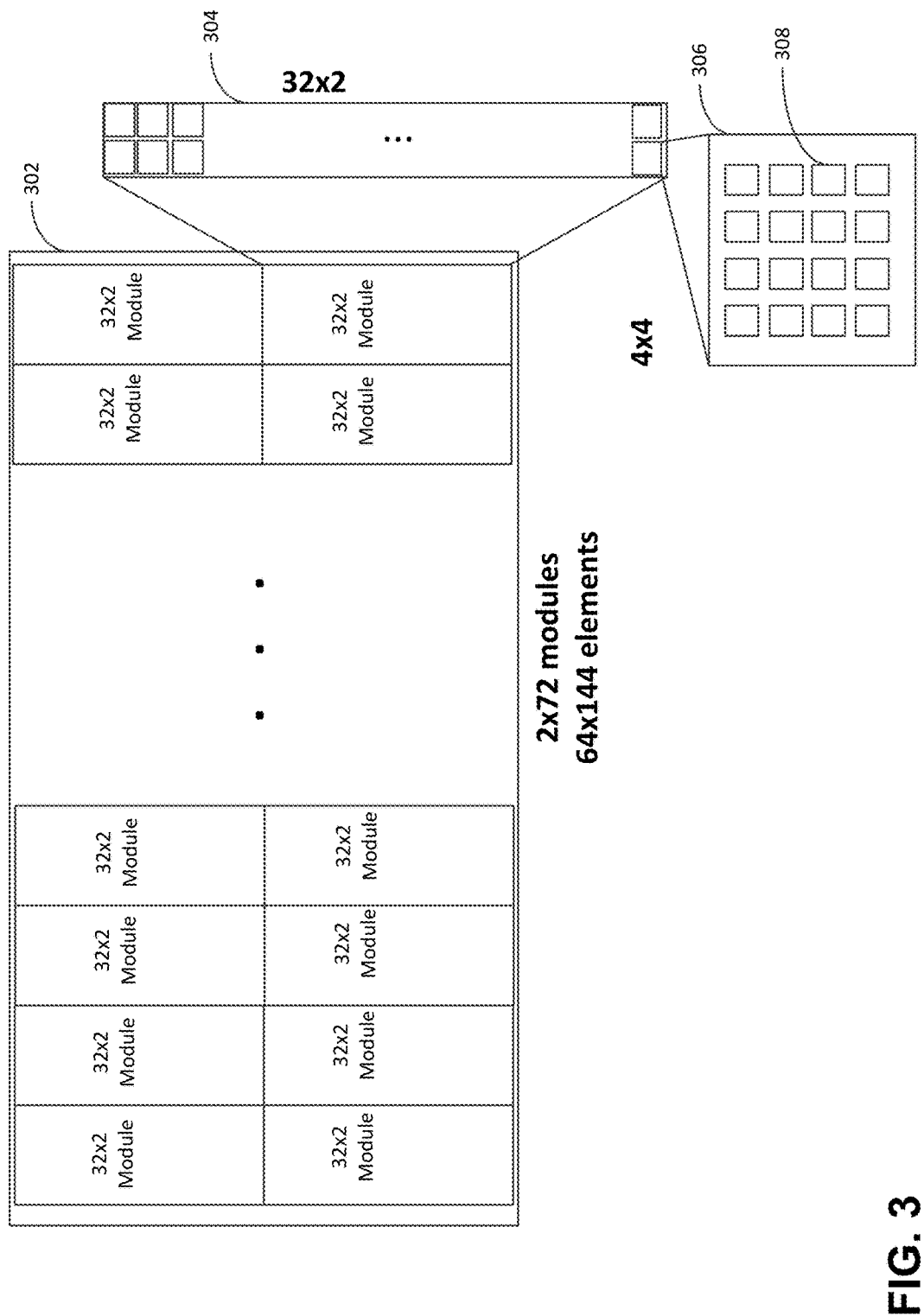
FIG. 3 shows an illustrative arrangement of ultrasonic transducers integrated with the substrate of a single substrate ultrasound device, in accordance with some embodiments of the technology described herein.

FIG. 3 shows substrate 302 (e.g., a semiconductor substrate) of an ultrasound device having multiple ultrasound circuitry modules 304 formed thereon. As shown, an ultrasound circuitry module 304 may comprise multiple ultrasound elements 306. An ultrasound element 306 may comprise multiple ultrasonic transducers 308.

In the illustrated embodiment, substrate 302 comprises 144 modules arranged as an array having two rows and 72 columns. However, it should be appreciated that a substrate of a single substrate ultrasound device may comprise any suitable number of ultrasound circuitry modules (e.g., at least two modules, at least ten modules, at least 100 modules, at least 1000 modules, at least 5000 modules, at least 10,000 modules, at least 25,000 modules, at least 50,000 modules, at least 100,000 modules, at least 250,000 modules, at least 500,000 modules, between two and a million modules, etc.) that may be arranged as an two-dimensional array of modules having any suitable number of rows and columns or in any other suitable way.

In the illustrated embodiment, each ultrasound circuitry module 304 comprises 64 ultrasound elements arranged as an array having 32 rows and two columns. However, it should be appreciated that an ultrasound circuitry module may comprise any suitable number of ultrasound elements (e.g., one ultrasound element, at least two ultrasound elements, at least four ultrasound elements, at least eight ultrasound elements, at least 16 ultrasound elements, at least 32 ultrasound elements, at least 64 ultrasound elements, at least 128 ultrasound elements, at least 256 ultrasound elements, at least 512 ultrasound elements, between two and 1024 elements, at least 2500 elements, at least 5,000 elements, at least 10,000 elements, at least 20,000 elements, between 1000 and 20,000 elements, etc.) that may be arranged as a two-dimensional array of ultrasound elements having any suitable number of rows and columns or in any other suitable way.

In the illustrated embodiment, each ultrasound element 306 comprises 16 ultrasonic transducers arranged as a two-dimensional array having four rows and four columns. However, it should be appreciated that an ultrasound element may comprise any suitable number of ultrasonic transducers (e.g., one, at least two, at least four, at least 16, at least 25, at least 36, at least 49, at least 64, at least 81, at least 100, between one and 200, etc.) that may be arranged as a two dimensional array having any suitable number of rows and columns (square or rectangular) or in any other suitable way.

It should be appreciated that any of the components described above (e.g., ultrasound transmission units, ultrasound elements, ultrasound transducers) may be arranged as a one-dimensional array, as a two-dimensional array, or in any other suitable manner.

In some embodiments, an ultrasound circuitry module may comprise circuitry in addition to one or more ultrasound elements. For example, an ultrasound circuitry module may comprise one or more waveform generators and/or any other suitable circuitry.

In some embodiments, module interconnection circuitry may be integrated with the substrate 302 and configured to connect ultrasound circuitry modules to one another to allow data to flow among the ultrasound circuitry modules. For example, the device module interconnection circuitry may provide for connectivity among adjacent ultrasound circuitry modules. In this way, an ultrasound circuitry module may be configured to provide data to and/or received data from one or more other ultrasound circuitry modules on the device.

Digital Signal Processing Circuitry

Figure 4:
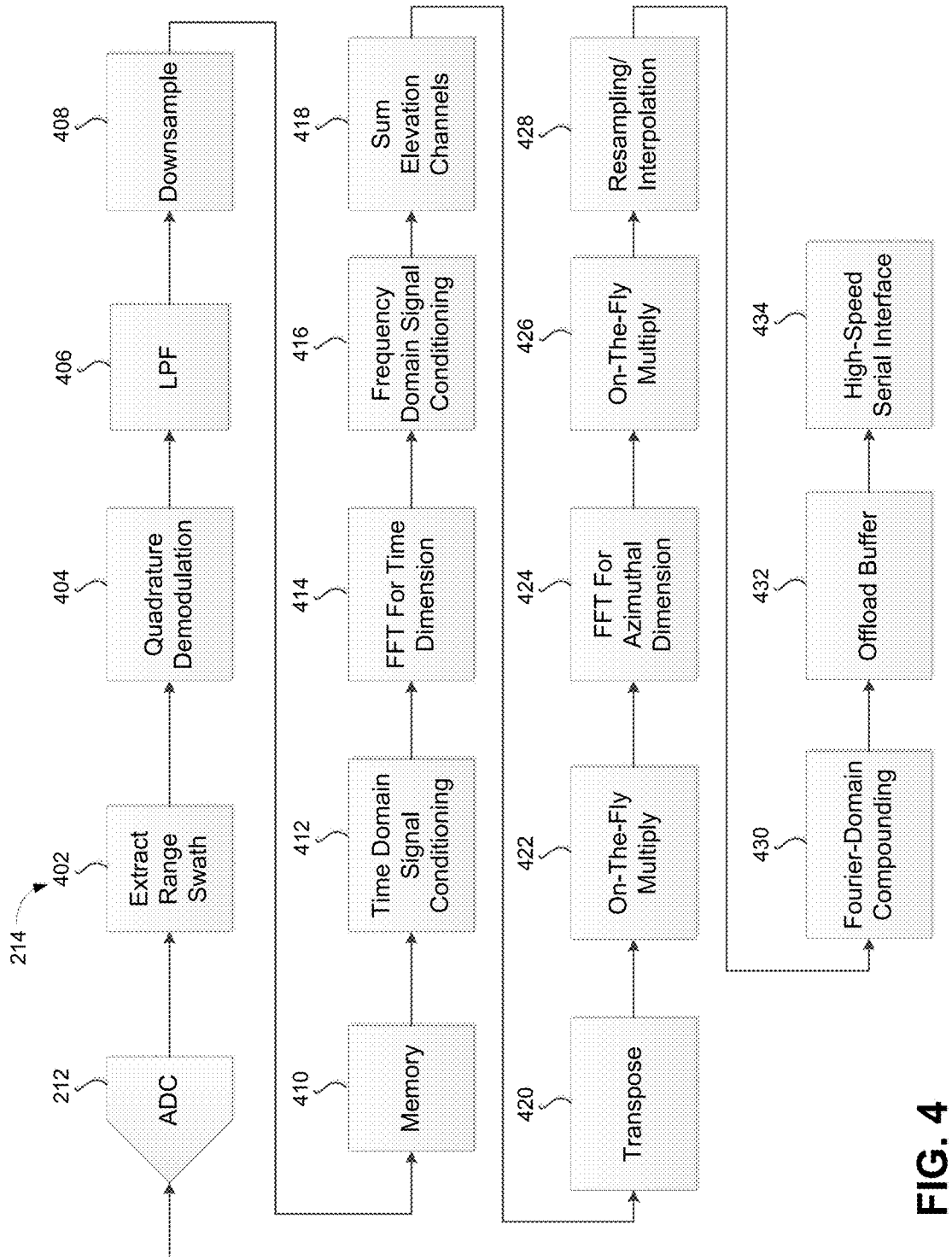
FIG. 4 is a block diagram of the digital processing block of the RX circuitry, in accordance with some embodiments of the technology described herein.

FIG. 4 is a block diagram of the digital processing block 214 of RX circuitry 106, in accordance with some embodiments of the technology described herein. The digital processing block 214 is configured as signal processing circuitry that receives digital signal samples from ADC 212, processes the signal samples, and provides the processed signal samples to a high-speed serial interface for subsequent use in image formation processing. The signal processing performed by block 214 may include, but is not limited to, processing for data reduction, data compression and/or downsampling, processing for compensation of various physical and circuit effects, and performing Fourier-domain compounding of data obtained over multiple different acquisitions.

As shown in FIG. 4, the signal processing circuit includes an extract range swath block 402, a quadrature demodulation block 404, a filter block 406 shown as a low pass filter (LPF), a downsample block 408, a memory 410, a time domain signal conditioning block 412, a fast Fourier transform (FFT) block 414, a frequency domain signal conditioning block 416, a sum elevation channels block 418, a transpose block 420, a first multiply block 422, a second FFT block 424, a second multiply block 426, a resampling/interpolation block 428, a Fourier-domain compounding block 430, offload buffer block 432, and high-speed serial interface block 434 to which the output of the signal processing chain may be supplied. In turn, data offloaded via the high-speed serial interface 434 may be used to form one or more images using any suitable image formation technique, as aspects of the technology described herein are not limited in this respect.

The signal processing circuit of FIG. 4 processes signals received via ADC 212 from a single ultrasound transducer element or a group of ultrasound transducer elements. Thus, at least a portion of the signal processing chain is repeated for each ultrasound transducer element or group of ultrasound transducer elements. For example, in some embodiments, blocks 402-410 may be repeated for each ultrasound transducer element or group of ultrasound transducer elements resulting in processed ultrasound data being stored in memory 410, after which blocks 412-434 may process ultrasound data stored in memory 410. Blocks 412-434 may be applied to all of the processed ultrasound data stored in memory 410 or repeatedly to portions of the processed data stored in memory 410 so that the processed ultrasound data stored in memory 410 is processed in chunks, on a time multiplexed basis. As one non-limiting example, blocks 402-410 may be repeated until data representing multiple acquisitions performed by the ultrasound device is stored in memory 410. Then blocks 412-434 may process data obtained during the multiple acquisitions (at once or in chunks), for example, by performing Fourier-domain compounding, as described in more detail below.

As may be appreciated from the foregoing, in some embodiments, a portion of the signal processing chain utilizes a reduced number of channels and processes the signals for several channels on a time multiplexed basis. By utilizing a reduced number of channels for signal processing, the chip area and power consumption can be reduced in comparison with a configuration that utilizes one signal processing channel for each ultrasound transducer element or group of ultrasound transducer elements. By way of example only, an ultrasound transducer array may include 1000 ultrasound transducer elements, thereby requiring 1000 signal processing channels. In some embodiments, the number of processing channels following memory 410 is reduced, as compared with the number of processing channels before memory 410. For example, 4, 8 or 16 channels may be used following memory 410, but the architecture is not limited with respect to the number of channels. As indicated, the memory 410 can be located at any point in the signal processing circuit to make an effective rate change via time multiplexing. It should also be appreciated that, in some embodiments, the signal processing circuit of FIG. 4 may be implemented without memory 410 by using a fully streaming architecture in which parallel processing hardware is used for parallel processing of data across multiple different channels (in some instances, without the use of time multiplexing).

The signal processing circuit of FIG. 4 can have a variety of configurations in which some blocks are bypassed or omitted, depending on the requirements of a particular ultrasound system. For example, the quadrature demodulation block 404, the filter block 406 and the downsample block 408 perform data reduction and may be bypassed or omitted in systems where data reduction is not required. As another example, the time-domain conditioning block 412 may be bypassed or omitted. As another example, the frequency-domain signal conditioning block may be bypassed or omitted. As another example, one or both of the multiply blocks 422 and 426 blocks may be bypassed or omitted. As another example, offload buffer 432 may be bypassed omitted. In some embodiments, any combination of the blocks listed above in this paragraph may be bypassed or omitted.

Extract Range Swath Block 402

The extract range swath block 402 selects input samples that contribute to the image and discards input samples that do not contribute to the image. In order to process an image whose pixels have a given extent and location relative to the aperture, and a waveform with a given pulse length is used, there is a set of time samples that will contribute to the image pixels for a given receiver/excitation combination; time samples outside this set may be discarded. In some embodiments, the extract range swath block 402 may be implemented by streaming of data from the ADC 212, wherein the selected range of data is defined by the beginning and ending times when the data is digitized and/or is injected into the signal processing circuit.

Extracting the contributing portion of the receive swath can reduce the data transfer requirements (when done onboard), the data storage requirements (whether in memory or writing to disk), and the processing burden. This can be done to various degrees of compactness depending on the importance of the data reduction. A basic implementation includes a constant time extent across all receivers and all excitations, with a constant start time across all receivers and all excitations. Other implementations can use a separate start time and time extent for each receiver and each excitation. After data transfer, the data are aligned and arranged in whatever form is necessary for processing.

There are usually nonzero receive A/D samples at times while the system is transmitting or shortly thereafter, resulting in highly distorted A/D values from saturation or other nonlinearities, despite any receiver protector circuitry or switching. These samples do not contribute to usable imagery and can cause many problems and artifacts in the imagery, which make it generally more difficult to do basic diagnostics. When performing any sort of deconvolution or other temporal frequency domain processing (often even just truncating to a processing band), the energy in the extended time domain may contaminate the entire image. Making estimates of the spectrum (either for diagnostics or calibration) with these samples present can be problematic, since the energy in these samples dominates the energy in the entire receive channel. Accordingly, in some embodiments, these samples may be discarded in block 402.

Data Reduction Blocks 404-408

In the embodiment of signal processing chain 214 illustrated in FIG. 4, data reduction is performed, at blocks 404-408, on samples selected by extract range swath block 402. As described above, in some configurations where data reduction is not used, blocks 404-408 may be bypassed or omitted. Where implemented, data reduction may be performed by performing quadrature demodulation at block 404, filtering at block 406, and downsampling at block 408.

In some embodiments, quadrature demodulation block 404 may be implemented as two separate data streams for the imaginary (I[n]) and quadrature (Q[n]) portions of the complex input signal x[n]. QDM block 404 may include a numerically-controlled oscillator, or any other suitable component, that may be used to generate $\cos(2\pi f_c t)$ and $\sin(2\pi f_c t)$, where the center frequency $f_c$ is selected to provide a particular amount of demodulation. Demodulation may phase modulate a signal to be centered at 0 Hz or bounded by some desired frequency range for filtering. In some embodiments, it may be desirable to match $f_c$ with a frequency of interest of the transducers that are used in the array(s) 102. The imaginary and quadrature data streams from QDM block 404 are further processed by filter block 406 and downsample block 408.

In the embodiment illustrated in FIG. 4, filter block 406 is illustrated as performing low-pass filtering (LPF). However, it should be appreciated that other types of filtering, such as band-pass filtering (BPF) and high-pass filtering (HPF) may alternatively be used in filter block 406.

In some embodiments, a cascade integrating comb (CIC) filter architecture may be used to perform filtering (e.g., for filter block 406) and decimation (e.g., for downsample block 408). For example, such a CIC filter architecture may be used to accurately calculate a range value using a precise delay time index. The CIC filter may include a plurality (N) stages and act as a low-pass filter, while decimating the input data stream x[n] to produce an output data stream y[n]. Increasing the number of stages may result in more droop in the passband, while increasing the number of stages results in better image rejection. In some instances, implementations, passband droop may be at least partially addressed using a compensation filter that is applied after the CIC filter has been applied to the data.

Memory 410

Referring again to FIG. 4, the memory 410 stores signal samples after the received signal samples are processed by the extract range swath block 402, the quadrature demodulation block 404, the low pass filter 406, and the downsample block 408. The signal samples stored in memory 410 may be indexed according to time. Accordingly, the signal samples may be written to memory 410 upon receipt from the ultrasound transducer array and after initial processing (e.g., by blocks 402, 404, 406, and 408). The signal samples may be read from memory 410 when required by the processing blocks following memory 410 (e.g., time-domain signal conditioning block 412 in implementations that include this block).

Figures 5A, 5B:
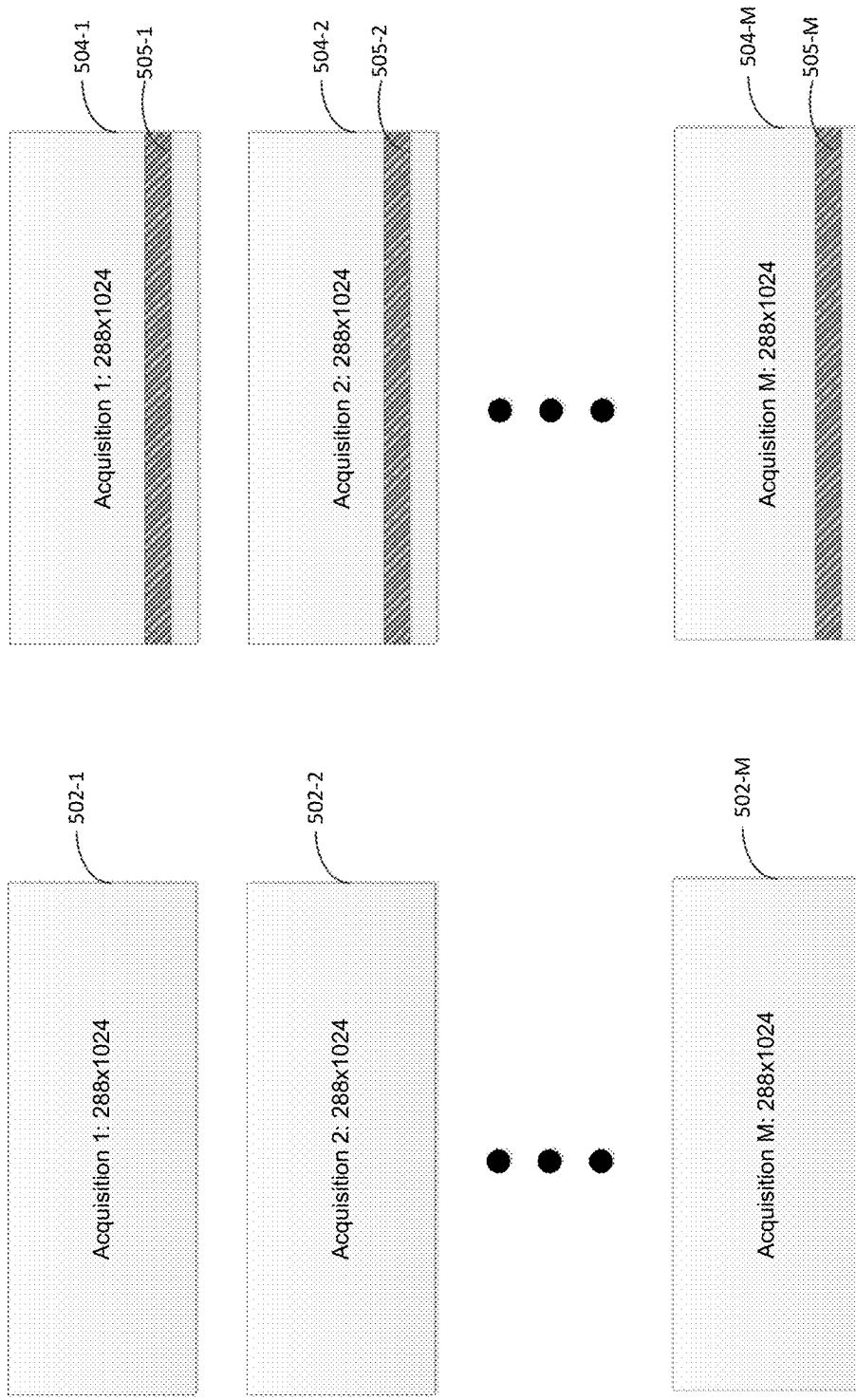

In some embodiments, signal samples obtained during each of multiple acquisitions may be stored in memory 410. For example, as shown in FIG. 5A, memory 410 may store M sets of signal samples (i.e., signal sample sets 502-1, 502-2, . . . , 502-M) corresponding to M respective acquisitions performed by the ultrasound transducer array, where M is any positive integer greater than or equal to one. In the illustrative example shown in FIG. 5A, each set of signal samples includes 1024 signal samples obtained over time for each of 288 channels. Data in each of the 288 channels may be obtained, for example, by combining data obtained by a group of ultrasound elements. For example, each of the 288 channels may correspond to a single column of ultrasound elements in a respective ultrasound module 304 (substrate 302 includes 144 total ultrasound modules each having two columns of ultrasound elements). Data in each of the 288 channels may be obtained, for example, by adding or averaging signal samples obtained by ultrasound elements in the corresponding column of the respective ultrasound module.

It should be appreciated that the example of FIG. 5A is illustrative and non-limiting, as each set of signal samples may include any suitable number of signal samples obtained for each of any suitable number of channels. Each channel may correspond to any suitable set of ultrasound elements of the ultrasound transducer array, as aspects of the technology described herein are not limited in this respect. Additionally, in some embodiments, signal samples in memory 410 may be indexed according to acquisition, time, and channel. However, in other embodiments, signal samples may be indexed in any other suitable way. Additionally, although each set of signal samples is shown in FIG. 5A as being organized as a two-dimensional array, this is for clarity presentation and not by way of limitation, as each set of signal samples may be organized (e.g., stored) in any other suitable way.

As described above, signal samples may be read from memory 410 when required by the processing blocks following memory 410. In some embodiments, signal sample sets corresponding to respective acquisitions may be read from memory 410 and processed by the processing blocks following memory 410. As described in more detail below, processing blocks 412-428 may process signal samples in each of the signal sample sets independently of one another (e.g., each of blocks 412-428 may process signal sample set 502-1 independently of signal sample set 502-2). Signal sample sets corresponding to respective acquisitions may be combined, as described below with reference to processing block 430, to perform Fourier-domain compounding.

In the embodiment illustrated in FIG. 4, memory 410 is provided between blocks 408 and 412. However, aspects of the technology described herein are not limited in this respect, as, in other embodiments, memory 410 may be provided between any pair of blocks or even sub-blocks (blocks within blocks). At any point in the processing circuit, a memory block may facilitate a reduction in the rate of streamed processing, thus reducing the number of parallel resources needed for processing (e.g., 1152 channels being processed concurrently may be saved to memory, then after memory the streaming processing may only consist of 4 channels at a time). One reason for reducing the streaming rate is to optimize between speed and resources by matching a data rate interface (e.g., universal serial bus (USB), Firewire, low voltage differential signaling (LVDS), Thunderbolt, etc.).

Time Domain Signal Conditioning Block 412

The time domain signal conditioning block 412 shown in FIG. 4 performs signal conditioning of the signal samples in the time domain. The signal conditioning may involve weighting of the time domain signals to compensate for various effects. The weighting may be performed using a weighting function or mask. The weighting function may include a coefficients, or weighting values, corresponding to a range of times following a reference time, such as a transmit event. Thus, for example, the signal samples may include samples at times $t_0, t_1, t_2, \ldots, t_n$ after a reference time, and the weighting function may include a coefficient, or a weighting value, corresponding to each signal sample after the reference time. Each signal sample may be multiplied by the corresponding coefficient to provide a weighted signal sample. The time domain signal conditioning block 412 may include a memory to store the coefficients of one or more the weighting functions. The weighting functions may be fixed or may be downloaded from a host computer to provide flexibility. The weighting functions may be channel dependent or channel independent. The multiplication of the signal samples by the weighting values can be a complex multiply.

The time domain signal conditioning block 412 may be configured to read signal samples from memory 410 and apply one or more weighting functions to the read signal samples. For example, block 412 may access a set of signal samples corresponding to an acquisition (e.g., set of signal samples 502-2) and apply one or more weighting function to samples in the set of signal samples. In block 412, a weighting function may be applied to a sequence of signal samples obtained over time for a particular channel (e.g., to signal samples in a particular row of set of signal samples 502-1 shown in FIG. 5A). Additionally or alternatively, a weighting function may be applied to a set of samples obtained at a same time across different channels (e.g., to signal samples in a particular column of the set of signal samples 502-1 shown in FIG. 5A).

In some embodiments, block 412 may perform a channel-independent (e.g., receiver and excitation independent) weighting of signal samples accessed from memory 410. When the only weighting to be applied across time is channel-independent, then there can be a savings of memory and a simplification in the indexing. When any other form of time-domain weighting (receiver-dependent, excitation-dependent, or channel-dependent) is used, this channel-independent weight can be absorbed into the other time-domain weighting. Non-limiting examples of channel-independent time domain weights include: (1) carrier frequency adjustment; (2) applying a linear phase to the samples; and (3) time-gain compensation (TGC), which in some cases may be performed using the same TGC profile for every receiver and every excitation.

In some embodiments, block 412 may perform a channel-dependent weighting of signal samples accessed from memory 410. Applying a channel-dependent weighting may include applying a receiver-dependent weighting function that does not depend on the excitation used to obtain the signal samples. For example, time-gain compensation may be performed using a different weighting function for each receiver (e.g., in a case where the variations in receiver amplifier gains are sufficiently large that they need to be dealt with separately). Additionally or alternatively, applying a channel-dependent weighting may include applying an excitation-dependent weighting function (e.g., in a case where different time-gain compensation settings are intentionally used to best quantize the signal across all excitations).

Although the quality of the resulting images may improve when the weighting performed at block 412 is dependent on the channel, excitation, and/or one or more other factors, implementing such a weighting may require additional power, processing, and/or memory resources. This tradeoff between image quality on the one hand and hardware size and power consumption on the other hand may be taken into account when implementing an ultrasound probe. In some embodiments, the probe may be configured to implement both a weighting with dependencies (e.g., on channel, on excitation, etc.) or without dependencies and a determination of which type of weighting to use may be made, during operation of the probe, based on available power, processing, and/or memory resources.

Fast Fourier Transform Block 414

In the embodiment illustrated in FIG. 4, the FFT block 414 receives signal samples, after weighting performed by time domain signal conditioning block 414, and performs FFT processing on the received signal samples. The FFT block 414 may apply a one-dimensional fast Fourier transform to the signal samples with respect to time by applying, for each channel, an FFT to the signal samples obtained over time on that channel. For example, block 414 may access a set of signal samples corresponding to an acquisition (e.g., set of signal samples 504-1) and perform an FFT on the signal samples in the set for each of the channels (e.g., apply an FFT to each row, for example row 505-1, of set of signal samples 504-1).

Thus, in some embodiments, the signal samples received at block 414 may include multiple groups of signal samples with each of the multiple groups corresponding to a respective channel in a plurality of respective channels. Each of the multiple groups, therefore, consists of signal samples obtained from data obtained over a respective channel. The FFT block 414 may apply a one-dimensional FFT to the signal samples by applying a one-dimensional FFT to each of the multiple groups. The complex-valued data obtained as a result of applying the one-dimensional FFT to the signal samples includes multiple groups of complex values each group of complex values corresponding to frequency/phase information in the data obtained over a respective channel.

In some embodiments, block 414 may apply a one-dimensional FFT to the signal samples with respect to time for each channel and for each acquisition. For example, as illustrated in FIG. 5B, block 414 may apply an FFT to each row of samples (e.g., including row 505-1) of set of signal samples 504-1, an FFT to each row of samples (e.g., including row 505-2) of set of signal samples 504-2, . . . , and to each row of samples (e.g., including row 505-M) of set of signal samples 504-M. In this example, sets of samples 504-1, 504-2, and 504-M may have been obtained from sets of samples 502-1, 502-2, and 502-M as a result of processing performed by time-domain signal conditioning block 412. After the FFT is performed, each row of sets 504-1, 504-2, . . . , 504-M represents frequency and phase values obtained through application of the fast Fourier transform. It should be appreciated that each row of signal samples shown in the example of FIGS. 5A-5F corresponds to signal samples obtained over time for a respective channel, and that the organization of the signal samples shown in FIGS. 5A-5F is not representative of and may be different from the layout of ultrasound elements in an ultrasound transducer array such as the layout shown in FIG. 3.

It should be appreciated that any FFT performed by block 414 may be performed by zero padding the signal samples to be transformed. The signal samples may be zero padded by placing the time domain data in the FFT-center of a zero-filled array of a larger, predetermined size. For example, although in the embodiment illustrated in FIG. 5B a 1024 point FFT is applied to each row of data having 1024 signal samples, in other embodiments, a 2048-point or a 4096-point FFT may be applied to each row of data having 1024 signal samples. In addition, the zero-padding may be channel independent (i.e., the same amount of zero padding is used for data in each channel) or channel dependent (i.e., different amounts of zero padding is used for data in different channels).

Additionally, in some embodiments, after an FFT is applied to a sequence of signal samples, the result may be truncated (in the frequency domain) such that only a selected portion of the resultant spectrum is used to for forming an image. Any portion of the resultant spectrum may be chosen (e.g., for a specified band, by removing high-frequencies, etc.).

Frequency Domain Signal Conditioning Block 416

The frequency domain signal conditioning block 416 receives frequency domain values, obtained as a result of processing performed by FFT block 414, and performs signal conditioning in the frequency domain. In particular, the frequency domain signal conditioning block 416 performs weighting of the frequency domain values to compensate for one or more effects and provides weighted frequency domain values. Block 416 may be configured to apply a weighting function to a sequence of signal samples obtained over time for a particular channel. For example, block 416 may be configured to applying a weighting function to signal samples in a particular row of set of signal samples 504-1 shown in FIG. 5B after an FFT has been applied to that particular row in FFT block 414. The same or different weighting functions may be applied to signal samples corresponding to different channels, as discussed in more detail below.

The processing performed by block 416 may be used to take into account many different physical effects by modeling each of the effects with a respective transfer function and using the transfer functions to cancel out the effects. Block 416 may also be used to perform motion compensation/phase adjustment.

Block 416 may be configured to use any suitable weighting(s) to perform frequency-domain weighting. For example, block 416 may be configured to use channel independent weighting(s), channel dependent weighting(s), or any suitable combination thereof. Examples of channel dependent weightings include receiver-dependent weightings and excitation-dependent weightings. There are many options and combinations for combining channel-independent and channel-dependent weightings. Some of these options and combinations are described below.

A channel-independent frequency domain weighting may be used to account for several effects, for example: (1) temporal frequency linear aperture weighting, chosen to impose a specific sidelobe structure in the imagery; (2) constant "master waveform" applied across all channels; and (3) common transducer transfer function.

In some embodiments, where at least one receiver/excitation/channel-dependent frequency domain weighting is applied within preprocessing, the channel-independent frequency domain weighting can be absorbed there. One possible exception may be when the receiver/excitation/channel-dependent frequency domain weighting is phase-only, where the phase is described by a low-order polynomial (such as motion compensations with linear phase or other phase adjustments with quadratic phase functions). In this case, the phase-only function can be efficiently computed on-the-fly, and the channel-independent weight is applied as a separate multiply step. This would incur more overall multiplies but save a large amount of memory that would be used for storing the pre-computed weights (particularly for fully channel-dependent weights).

Receiver-dependent frequency domain weighting may be applied in some instances. This may done in cases where the transfer functions of each combined transmitter/transducer/receiver are different enough to warrant accounting for them separately.

Excitation-dependent frequency domain weighting may be applied to the data that is receiver-independent. A relevant example is for plane wave excitations, where there is often an offset delay relative to the phase reference at the middle receiver that is a function of the plane wave angle. While this can be absorbed into a time domain interpolation or a fully channel-dependent frequency domain weighting, the amount of memory storage for a full set of weights may make an excitation-dependent weighting attractive.

Channel-dependent frequency domain weighting may also be utilized. The most general weighting is one that is potentially different on every channel of data, where a channel corresponds a unique receiver/excitation combination. Any channel-independent weightings can be absorbed into channel-dependent, receiver-dependent, or excitation-dependent weightings.

When using a receiver-dependent weighting and an excitation-dependent weighting, there may a tradeoff between the additional storage required to absorb both weightings into a single channel-dependent weighting versus using less storage with two separate multiplies. In addition, there may be a tradeoff between the amount of memory to store coefficients of the multiplication versus the logic required to generate these parameters on-the-fly. Significant savings on memory may be achieved with an on-the-fly coefficient generation approach, enabling quality processing on low-cost hardware.

There may be a need to provide frequency-independent, time/range independent, but channel-dependent weightings. The most common type of this weighting is a scalar gain that is different from receiver-to-receiver, but is constant across excitation. These weights would likely have the fewest number of coefficients (since fast-time A/D samples dominate over the number of receivers), but if every complex multiply is expensive, then these types of weights can be absorbed into the other channel-dependent weights in whatever way is most appropriate (in fast-time or along frequency, depending on which one has a corresponding weight set that has the same receiver/excitation/channel dependence). If there are no receiver/excitation/channel-dependent corrections anywhere within preprocessing, then the tradeoff could be made between having a separate multiply stage vs. storage of fully channel-dependent weights where these fast-time/frequency-independent weights can be absorbed.

Reduction of localized acoustic energy as it propagates through tissue can be significant. It may be desirable to unweight the raw data with an estimated range-dependent profile in order to level out the image. It may be useful to compensate for approximate range decay. In particular, many 2-D imaging formulations assume infinite line sources and infinite line transducer elements, which result in cylindrical wave decay. Many of these formulations actually impose the correct cylindrical wave behavior on the raw data (when used in the forward sense, and accurately removed when used in the "inverse" sense). But since the actual transducers behave more like point sources and the volume is composed of point scatterers, spherical waves are more appropriate to describe basic propagation loss.

The signal attenuation characteristics through tissue are not generally known in advance. Approximating the attenuation as a homogeneous process with estimated parameters, however, can aid in leveling out the image brightness as a function of downrange. Even with assumed homogeneous attenuation parameters, the attenuation should be imposed/removed as a function of frequency, either through polynomial or other basis expansion, multirate, or by other means. If this is too computationally burdensome, then it can be approximated using the parameters at a single frequency.

Sum Elevation Channels Block 418

Data processed by frequency domain signal conditioning block 416 is provided to sum elevation channels block 418, which sums elevation channel data in the frequency domain. The sum may be weighted or unweighted. Block 418 may sum elevation channel data for each acquisition. In some embodiments, block 418 may be omitted and channel data for each acquisition may not be summed across elevation. Additionally, in some embodiments, any of the previously-described blocks may apply a time-domain delay to the signal either in the time-domain or via a frequency modulation multiplication in the frequency-domain. Such time-domain delays may create a receive beam pattern in elevation when summed, which may be a focused beam, for example.

The manner in which processing is performed by sum elevation channels block 418 may be appreciated with reference to FIGS. 5B and 5C. After FFT and frequency domain signal conditioning is performed by blocks 414 and 416 on sets of signal samples 504-1, 504-2, . . . , 504-M (shown in FIG. 5B), each resulting set of signal samples may include 288×1024 complex values (288 channels with 1024 complex values representing frequency and phase for each channel). The first 144 channels may represent columns of ultrasound elements in the top portion of (i.e., first row of the ultrasound modules in) substrate 302 shown in FIG. 3. The second 144 channels may represent columns in the bottom portion of (i.e., second row of the ultrasound modules in) substrate 302 shown in FIG. 3. In this example, block 418 may sum the frequency data for the first 144 channels with the frequency data for the second 144 channels to obtain 144×1024 complex values (144 channels with 1024 complex values representing frequency and phase for each channel). This is illustrated in FIG. 5C, where sets of complex values 506-1, 506-2, . . . , 506-M (each containing 144×1024 complex values) are obtained by summing (in block 418) frequency data for the first 144 channels with the frequency data for the second 144 channels.

Transpose Block 420

In embodiments where sets of signal samples corresponding to respective acquisitions are stored in arrays (or any suitable data structure effecting a two-dimensional indexing of complex values), transpose block 420 may reorganize the sets of signal samples to transpose them. Thus, if a set of signal samples corresponding to an acquisition is organized (e.g., stored in, indexed via, etc.) in a 144×1024 array of complex values, after transposition, the set of signal samples is organized in a 1024×144 array of complex values. This processing may reduce the computational load of performing a cross-range FFT at block 424 (described below) such that the FFT may be efficiently applied to rows of the data structure used to store the signal samples. In some embodiments, the processing performed at this stage may be accomplished with streaming and without penalty through organized reading and writing to a buffer.

Multiply Blocks 422 and 426

Multiply blocks 422 and 426 may be used to efficiently apply weightings in the frequency domain to the data before (in block 422) and after (in block 426) performing cross-range or azimuthal FFT processing of the data in block 424, as described below. The multiply blocks 422 and 426 may be implemented using an on-the-fly multiply architecture, in some embodiments. These weightings may be used to compensate for any of numerous effects examples of which are provided above. The multiply blocks 422 and 426 may be used to multiply the signal samples with weights determined as a function of channel, frequency, excitation, and/or any other suitable factors.

In some embodiments, the first multiply block 422 may be used to adjust the overall stand-off or backpropagation distances, temporal frequency domain filtering, cross-range apodization, and/or any suitable factors as a function of parameters. The first multiply block 422 may be used to apply additional coefficients using fewer resources by doing coefficient calculations in the transpose direction (e.g., calculated values can be reused in one-direction more than in another).

In some embodiments, the second multiply block 426 may be used to adjust the cross-range frequency-domain filtering, diffraction kernel multiplication (a frequency-based diffraction propagation), evanescent wave filtering, or any suitable factors as a function of parameters.

Fast Fourier Transform Block 424

In the embodiment illustrated in FIG. 4, the FFT block 424 receives data, after any weighting performed by block 422, and performs FFT processing on the received data. In particular, FFT block 424 applies a one-dimensional fast Fourier transform to the complex-valued data with respect to the cross-range or azimuth direction.

As may be appreciated from the foregoing, in some embodiments, data received at block 424 may include data for each of multiple acquisitions. Data for each acquisition may include a set of complex values (e.g., 1024 complex values representing phase and frequency for 1024 corresponding frequency bins) for each of multiple channels (e.g., for each of 144 channels). In such embodiments, the FFT block 424 may apply a one-dimensional FFT across channels for each frequency bin thereby effecting a one-dimensional fast Fourier transform of the data with respect to the cross-range or azimuth direction. As discussed above, each of the 144 channels may correspond to ultrasound elements arranged in a respective column on substrate 302, shown in FIG. 3. When the substrate is disposed parallel to a face of the ultrasound probe that is used to perform imaging, the columns run left-to-right of the face of the ultrasound probe, which corresponds to the cross-range or azimuthal direction. For this reason, performing a one-dimensional FFT across channels for each frequency bin is referred to herein as performing a cross-range or azimuthal FFT.

For example, as shown in FIG. 5D, FFT block 424 may obtain data corresponding to acquisition (e.g., data 508-1 corresponding to an acquisition) and perform a one-dimensional FFT on a column of complex values 507-1 that contains complex values for a single frequency bin across multiple channels. It should be appreciated that although FIG. 5D shows complex values for a single frequency bin across multiple channels as being organized in a column, when transpose block 420 is included, these complex values may be organized in a row.

Accordingly, the complex-valued data provided to FFT block 424 may include multiple groups of complex values, each of the multiple groups of complex values corresponding to a respective frequency bin in a plurality of frequency bins. The FFT block 424 may process the complex-valued data by applying a one-dimensional FFT to each of the multiple groups of complex values to obtain transformed complex values that are to be used by the Fourier compounding block as discussed below.

In some embodiments, FFT block 424 may apply a one-dimensional FFT to the signal samples with respect to channels for each frequency bin and for each acquisition. For example, as illustrated in FIG. 5D, block 424 may apply a one-dimensional FFT to each column of complex values (including column 507-1) of set of complex values 508-1, an FFT to each column of complex values (including column 507-2) of set of complex values 508-2, . . . , and to each column of samples (including column 507-M) of set of complex values 508-M. In this example, sets of complex values 508-1, 508-2, and 508-M may have been obtained from sets of complex values 506-1, 506-2, and 506-M as a result of processing performed by multiply block 422.

It should be appreciated that any FFT performed by FFT block 424 may be performed by zero padding the data to be transformed. The data may be zero padded by placing the data in the FFT-center of a zero-filled array of a larger, predetermined size. For example, although in the embodiment illustrated in FIG. 5D, each column of data includes 144 complex values, a 2048-point FFT may be applied to each column of data. As shown in FIG. 5E this results in sets of complex values 510-1, 510-2, . . . , 510-M each having 2048×1024 complex values. Each of these sets of complex values is obtained from data gathered during a respective acquisition.

In addition, the zero-padding may be channel independent (i.e., the same amount of zero padding is used for data in each channel) or channel dependent (i.e., different amounts of zero padding is used for data in different channels).

Resample/Interpolation Block 428

In some scenarios, after performing the FFT block 424, and optionally a multiply in block 426, it may be necessary to resample the resulting data. The resampling may be used to implement a resampling map from the Fourier space of the data collected from the sensor to the Fourier space of the object being imaged. This resampling map may be obtained from the dispersion relation. Accordingly, the resampling/interpolation block 428 may be used to map the temporal- and cross-range frequency to spatial longitudinal frequencies and spatial lateral frequencies. The resulting samples may be spaced evenly in the space of the object being imaged. As such, in some instances, the resampling operation performed by block 428 may transform an even sample spacing to a new sample spacing having an uneven set of samples.

Fourier Compounding Block 430

At Fourier compounding block 430, data corresponding to multiple different acquisitions is combined, sometimes termed compounded, in the Fourier domain. In particular, sets of complex values, each obtained from data gathered during a respective acquisition, are combined to produce a single set of Fourier compounded values. The sets of complex values may be combined in any suitable way and, for example, may be combined through an unweighted summation or a weighted summation (e.g., an average). Accordingly, the set of Fourier compounded values may be obtained as a (weighted or unweighted) linear combination of multiple sets of complex values each of which corresponds to a respective acquisition. In turn, the set of Fourier compounded values may be used to form an ultrasound image using any suitable image formation technique (e.g., inverse Fourier transform).

For example, the sets of complex values 510-1, 510-2, . . . , 510-M, shown in FIG. 5E and each containing 2048×1024 complex values, may be combined to obtain a single set of complex values 512 containing 2048×1024 complex values. As such set of complex values 512 may be obtained as a weighted or unweighted linear combination of M sets of complex values each of which is obtained from signal samples obtained from a respective acquisition.

Although in this illustrative example, M sets of complex values corresponding to M different acquisitions were compounded in the Fourier domain to obtain a single set of complex values, in other embodiments, not all acquisitions are compounded to produce a single compounded data set. For example, in some embodiments, data sets corresponding to one group of respective acquisitions may be compounded to obtain one compounded data set that may be subsequently used to produce one ultrasound image, and data sets corresponding to another group of respective acquisitions may be compounded to obtain another compounded data set that may be subsequently used produce another ultrasound image.

Offload Buffer 432 and High-Speed Interface 434

After Fourier domain compounding is performed at block 430, the resulting compounded data is provided via offload buffer 432 and high-speed interface 434 to another device for subsequent processing in furtherance of image formation. Offload buffer 432 is optional, but when used may reduce the bandwidth requirements for offloading data via high-speed interface 434. High-speed interface may be any suitable high-speed digital interface for offloading digital data and, for example, may be a USB 3.0 interface or a Thunderbolt interface. As noted above, the use of a high-speed serial data link to offload a digital data stream is one of the features that helps facilitate an "ultrasound on a chip" solution according to some embodiments of the technology described herein.

Digital Signal Processing Methods

Figure 6:
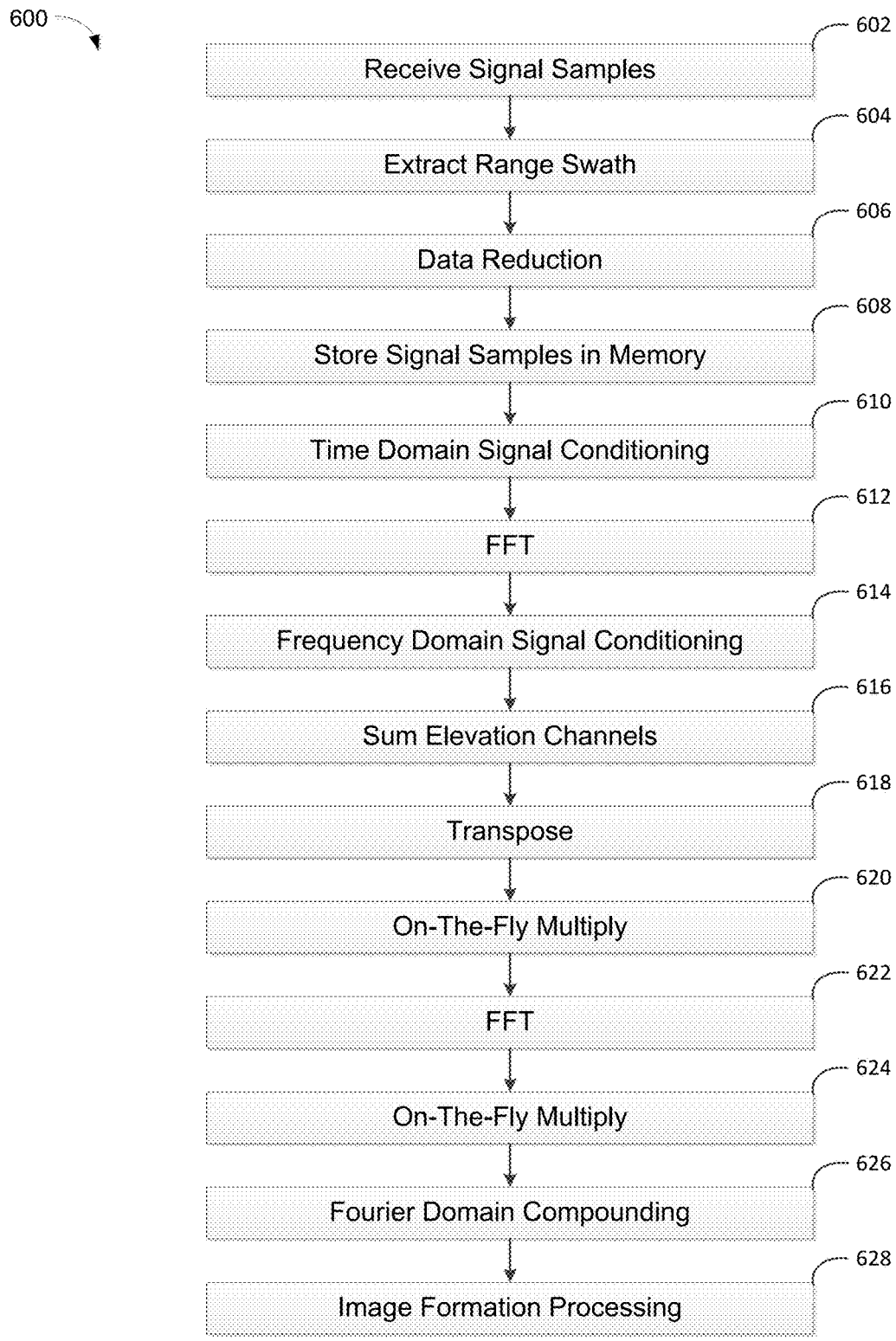
FIG. 6 is a flowchart of an example of a signal processing method to perform Fourier-domain compounding, in accordance with some embodiments of the technology described herein.

A flowchart of illustrative process 600 that is an example of a method performed by the digital signal processing circuitry of FIG. 4 is shown in FIG. 6. In stage 602, the digital signal processing circuitry receives signal samples from ADC 212. In stage 604, signal samples that do not contribute to the image may be discarded using extract range swath block 402. Non-linear signal samples may also be discarded. In stage 606, data reduction may be performed by using quadrature demodulation block 404 to perform quadrature demodulation, filtering block 406 to perform low pass filtering, and downsample block 408 to perform downsampling. The partially processed signal samples may then be stored in memory 410 in stage 608.

In stage 610, data values are read from memory 410 and time domain signal conditioning is performed by time domain signal conditioning block 412. As described above, time domain signal conditioning may include application of one or more weighting functions to the time domain signals. In stage 612, a one-dimensional fast Fourier transform is applied to the signal samples with respect to time using FFT block 414. The signal samples may include multiple groups of signal samples, each of the multiple groups being associated with a respective channel and applying the one-dimensional FFT to the signal samples may include applying the one-dimensional FFT to each of the multiple groups of signal samples with respect to time. In stage 614, frequency domain conditioning block 416 is used to perform frequency domain signal conditioning on the complex-valued data obtained at stage 612 via application of the one-dimensional FFT. As described above, frequency domain signal conditioning may include application of one or more frequency domain weighting functions to the frequency domain data. In stage 616, the elevation channels are summed by sum elevation channels block 418, thereby reducing the quantity of data supplied for image formation processing.

In stage 618, the complex-valued data may be transposed using transpose block 420, and an on-the-fly multiply may be performed in stage 620 using multiply block 422. In stage 622, FFT block 424 may be used to apply a one-dimensional FFT to the complex-valued data with respect to the cross-range or azimuth direction. The complex-valued data may include multiple groups of complex values each of the multiple groups being associated with a respective frequency bin in a plurality of frequency bins. Applying the one-dimensional FFT in stage 622 may include applying the one-dimensional FFT to each of the multiple groups of complex values. In stage 624, a multiply may be performed using multiply block 426 and resampling/interpolation may be performed by resampling/interpolation block 428, in stage 428. In stage 626, Fourier domain compounding is performed by Fourier domain compounding block 626. As described above, Fourier domain compounding may include combining, in the Fourier domain, data obtained from multiple different acquisitions. In stage 628, the Fourier compounded data is utilized for image formation processing.

In the process 600 of FIG. 6, optional functions may be omitted. For example, data reduction operations performed in stage 606 may be omitted. Additionally or alternatively, one or more of stages 610, 614, 616, 618, 620, and 624 may be omitted. Furthermore, additional steps may be included within the process 600 illustrated in FIG. 6.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code can be executed on any suitable processor or collection of processors, whether provided in a single computer or distributed among multiple computers.

Further, it should be appreciated that a computer may be embodied in any of a number of forms, such as a rackmounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. An ultrasound device, comprising:
   a semiconductor die;
   a plurality of micromachined ultrasonic transducer elements integrated on the semiconductor die and configured to output electrical signals in response to detecting ultrasound signals;
   transmit circuitry coupled to the plurality of micromachined ultrasonic transducer elements and configured to drive the plurality of micromachined ultrasonic transducer elements to generate ultrasound signals; and
   receive circuitry coupled to the plurality of micromachined ultrasonic transducer elements and configured to:
   obtain, over a first time period, based on first electrical signals provided by the plurality of micromachined ultrasonic transducer elements, a first set of signal samples representing a first acquisition;
   obtain, over a second time period different than the first time period, based on second electrical signals provided by the plurality of micromachined ultrasonic transducer elements, a second set of signal samples representing a second acquisition;
   apply a Fourier transformation to the first set of signal samples to generate a first Fourier-transformed set of signals and to the second set of signal samples to generate a second Fourier-transformed set of signals; and
   generate a Fourier-compounded set of signals at least in part by combining, in a Fourier domain, the first and second Fourier-transformed sets of signals.

2. The ultrasound device of claim 1, wherein the receive circuitry is further configured to:
   obtain, over a third time period different than the first time period and different than the second time period, based on third electrical signals provided by the plurality of ultrasonic micromachined transducer elements, a third set of signal samples representing a third acquisition;
   apply the Fourier transformation to the third set of signal samples to generate a third Fourier-transformed set of signals; and generate the Fourier-compounded set of signals at least in part by combining, in the Fourier domain, the first, second, and third Fourier-transformed sets of signals.

3. The ultrasound device of claim 1, wherein the first set of signal samples comprises a plurality of groups of signal samples, each of the plurality of groups of signal samples being associated with a respective channel in a plurality of channels.

4. The ultrasound device of claim 3, wherein the receive circuitry is configured to apply the Fourier transformation to the first set of signal samples at least in part by:
applying a first one-dimensional fast Fourier transformation (FFT) with respect to time to the first set of signal samples to obtain complex-valued data, the applying comprising applying the first one-dimensional FFT with respect to time to each of the plurality of groups of signal samples.

5. The ultrasound device of claim 4, wherein the receive circuitry is further configured to:
apply a time-domain weighting to the first set of signal samples before applying the first one-dimensional FFT to the first set of signal samples.

6. The ultrasound device of claim 4,
wherein the complex-valued data comprises a plurality of groups of complex values, each of the plurality of groups of complex values associated with a respective frequency bin in a plurality of frequency bins, and
wherein the receive circuitry is configured to apply the Fourier transformation to the first set of signal samples at least in part by applying a second one-dimensional FFT to the complex-valued data with respect to cross-range, the applying comprising applying the second one-dimensional FFT to each of the plurality of groups of complex values.

7. The ultrasound device of claim 6, wherein the receive circuitry is further configured to:
apply a frequency-domain weighting to the complex-valued data before applying the second one-dimensional FFT to the complex-valued data.

8. The ultrasound device of claim 1, wherein the first Fourier-transformed set of signals comprises a first plurality of complex values, wherein the second Fourier-transformed set of signals comprises a second plurality of complex values, and wherein combining the first and second Fourier-transformed sets of signals comprises summing complex values in the first plurality of complex values with respective complex values in the second plurality of complex values.

9. A method performed by an ultrasound device, the ultrasound device comprising a semiconductor die, a plurality of micromachined ultrasonic transducer elements integrated on the semiconductor die and configured to output electrical signals in response to detecting ultrasound signals, and receive circuitry coupled to the plurality of micromachined ultrasonic transducer elements, the method comprising using the receive circuitry to perform:
obtaining, over a first time period, based on first electrical signals provided by the plurality of micromachined ultrasonic transducer elements, a first set of signal samples representing a first acquisition;
obtaining, over a second time period different than the first time period, based on second electrical signals provided by the plurality of micromachined ultrasonic transducer elements, a second set of signal samples representing a second acquisition;
applying a Fourier transformation to the first set of signal samples to generate a first Fourier-transformed set of signals and to the second set of signal samples to generate a second Fourier-transformed set of signals; and
generating a Fourier-compounded set of signals at least in part by combining, in the Fourier domain, the first and second Fourier-transformed sets of signals.

10. The method of claim 9, further comprising using the receive circuitry to perform:
obtaining, over a third time period different than the first time period and different than the second time period, based on third electrical signals provided by the plurality of ultrasonic micromachined transducer elements, a third set of signal samples representing a third acquisition;
applying the Fourier transformation to the third set of signal samples to generate a third Fourier-transformed set of signals; and
generating the Fourier-compounded set of signals at least in part by combining, in a Fourier domain, the first, second, and third Fourier-transformed sets of signals.

11. The method of claim 9, wherein the first set of signal samples comprises a plurality of groups of signal samples, each of the plurality of groups of signal samples being associated with a respective channel in a plurality of channels.

12. The method of claim 11, wherein applying the Fourier transformation to the first set of signal samples further comprises:
applying a first one-dimensional fast Fourier transformation (FFT) with respect to time to the first set of signal samples to obtain complex-valued data, the applying comprising applying the first one-dimensional FFT with respect to time to each of the plurality of groups of signal samples.

13. The method of claim 12, further comprising:
applying a time-domain weighting to the first set of signal samples before applying the first one-dimensional FFT to the first set of signal samples.

14. The method of claim 12, wherein the complex-valued data comprises a plurality of groups of complex values, each of the plurality of groups of complex values associated with a respective frequency bin in a plurality of frequency bins, and wherein applying the Fourier transformation to the first set of signal samples further comprises applying a second one-dimensional FFT to the complex-valued data with respect to cross-range, the applying comprising applying the second one-dimensional FFT to each of the plurality of groups of complex values.

15. The method of claim 14, further comprising:
applying a frequency-domain weighting to the complex-valued data before applying the second one-dimensional FFT to the complex-valued data.

16. The method of claim 9, further comprising resampling the first Fourier-transformed set of signals and the second Fourier-transformed set of signals before combining the first and second Fourier-transformed sets of signals.

* * * * *